US009125589B2

(12) United States Patent
Sørnes

(10) Patent No.: US 9,125,589 B2
(45) Date of Patent: Sep. 8, 2015

(54) SYSTEM AND METHOD FOR TISSUE CHARACTERIZATION USING ULTRASOUND IMAGING

(75) Inventor: Anders Rasmus Sørnes, Oslo (NO)

(73) Assignee: General Electric Company, Schenectady, NY (US)

( * ) Notice: Subject to any disclaimer, the term of this patent is extended or adjusted under 35 U.S.C. 154(b) by 1622 days.

(21) Appl. No.: 11/801,322

(22) Filed: May 9, 2007

(65) Prior Publication Data

US 2008/0281196 A1 Nov. 13, 2008

(51) Int. Cl.
*A61B 8/00* (2006.01)
*A61B 8/08* (2006.01)
*A61B 5/02* (2006.01)

(52) U.S. Cl.
CPC .............. *A61B 8/08* (2013.01); *A61B 5/02007* (2013.01); *A61B 8/485* (2013.01)

(58) Field of Classification Search
CPC ........................... A61B 8/085; A61B 5/02007
USPC .......................... 600/443, 437, 438, 447, 459
See application file for complete search history.

(56) References Cited

U.S. PATENT DOCUMENTS

| | | | |
|---|---|---|---|
| 4,858,201 A * | 8/1989 | Goins et al. ...................... 367/75 |
| 5,197,475 A * | 3/1993 | Antich et al. .................. 600/437 |
| 5,549,111 A * | 8/1996 | Wright et al. .................. 600/443 |
| 5,606,971 A * | 3/1997 | Sarvazyan ..................... 600/438 |
| 5,810,731 A | 9/1998 | Sarvazyan et al. |
| 6,135,960 A | 10/2000 | Holmberg |
| 6,385,474 B1 * | 5/2002 | Rather et al. .................. 600/407 |
| 6,702,745 B1 | 3/2004 | Smythe |
| 6,876,928 B2 * | 4/2005 | Van Riel et al. .................. 702/2 |
| 7,175,599 B2 | 2/2007 | Hynynen et al. |
| 7,252,004 B2 | 8/2007 | Fink et al. |
| 7,670,293 B2 * | 3/2010 | Dubberstein et al. ......... 600/453 |
| 2004/0064050 A1 * | 4/2004 | Liu et al. ....................... 600/457 |
| 2004/0167403 A1 * | 8/2004 | Nightingale et al. ......... 600/437 |
| 2004/0215075 A1 * | 10/2004 | Zagzebski et al. ............ 600/442 |

FOREIGN PATENT DOCUMENTS

WO    WO 2007021185 A1 *    2/2007

* cited by examiner

*Primary Examiner* — Rajeev Siripurapu
(74) *Attorney, Agent, or Firm* — Dean D. Small; The Small Patent Law Group, LLC

(57) ABSTRACT

An ultrasound system comprises an ultrasound probe for transmitting transmit beams and receiving receive beams. A processor controls the ultrasound probe to direct the transmit beams in a first direction to acquire a first incidence frame of data and a second direction to acquire an second incidence frame of data, wherein the first and second directions are different with respect to each other. A tissue characterization module compares the normal and oblique incidence frames of data to determine at least one property parameter of a scanned medium based on amplitude differences between the receive beams.

31 Claims, 5 Drawing Sheets

SYSTEM AND METHOD FOR TISSUE CHARACTERIZATION USING ULTRASOUND IMAGING

BACKGROUND OF THE INVENTION

This invention relates generally to ultrasound imaging, and more particularly to detecting and indicating differences in tissue within an ultrasound image.

With current ultrasound imaging it is difficult to detect tissue properties such as tissue elasticity, stiffness, morphology or type. Tissue elasticity varies, for example, between different types of tissue, such as hard and soft plaque within the carotid artery. Also, a tumor or other mass will have tissue elasticity that is different compared to surrounding tissues. Having the ability to detect the elasticity or stiffness differences would improve the ability to detect dangerous plaque as well as other pathologies.

Shear modulus is a parameter related to the hardness or elasticity of a material or tissue. The shear modulus of various soft tissues ranges over several orders of magnitude. Previous methods for imaging elastic properties with ultrasound, such as radiation force ultrasound, rely on high amplitude, low frequency acoustic radiation fields or external vibration sources to generate shear waves in the tissue. Examples of imaging techniques are tissue velocity imaging (TVI) and strain imaging. Other techniques use multiple ultrasound transducers, thereby increasing the cost and complexity of a procedure.

Therefore, a need exists for detecting elasticity properties of tissues and indicating elasticity differences using standard ultrasound imaging with a single ultrasound probe.

BRIEF DESCRIPTION OF THE INVENTION

In one embodiment, an ultrasound system comprises an ultrasound probe for transmitting transmit beams and receiving receive beams. A processor controls the ultrasound probe to direct the transmit beams in a first direction to acquire a first incidence frame of data and a second direction to acquire an second incidence frame of data, wherein the first and second directions are different with respect to each other. A tissue characterization module compares the first and second incidence frames of data to determine at least one property parameter of a scanned medium based on amplitude differences between the receive beams.

In another embodiment, a method for detecting differences in tissue comprises acquiring a normal incidence frame of data by transmitting transmit beams in a first direction that is approximately 90 degrees with respect to a probe face. An oblique incidence frame of data is acquired by transmitting transmit beams in a second direction that is different than the first direction. The second direction forms an oblique angle with respect to the probe face. Amplitude magnitude differences are determined between receive beams of the normal and oblique incidence frame of data, and a representation is displayed based on amplitude magnitude differences.

In yet another embodiment, a method for detecting differences in tissue comprises acquiring a normal incidence frame of data by transmitting transmit beams in a first direction that is approximately 90 degrees with respect to a probe face. An oblique incidence frame of data is acquired by transmitting transmit beams in a second direction that is different than the first direction. The second direction forms an oblique angle with respect to the probe face. An image is displayed based on at least the normal incidence frame, and a parametric overlay is displayed on the image. The parametric overlay is based on amplitude differences between the normal and oblique incidence frames of data.

DETAILED DESCRIPTION OF THE INVENTION

Figure 1:
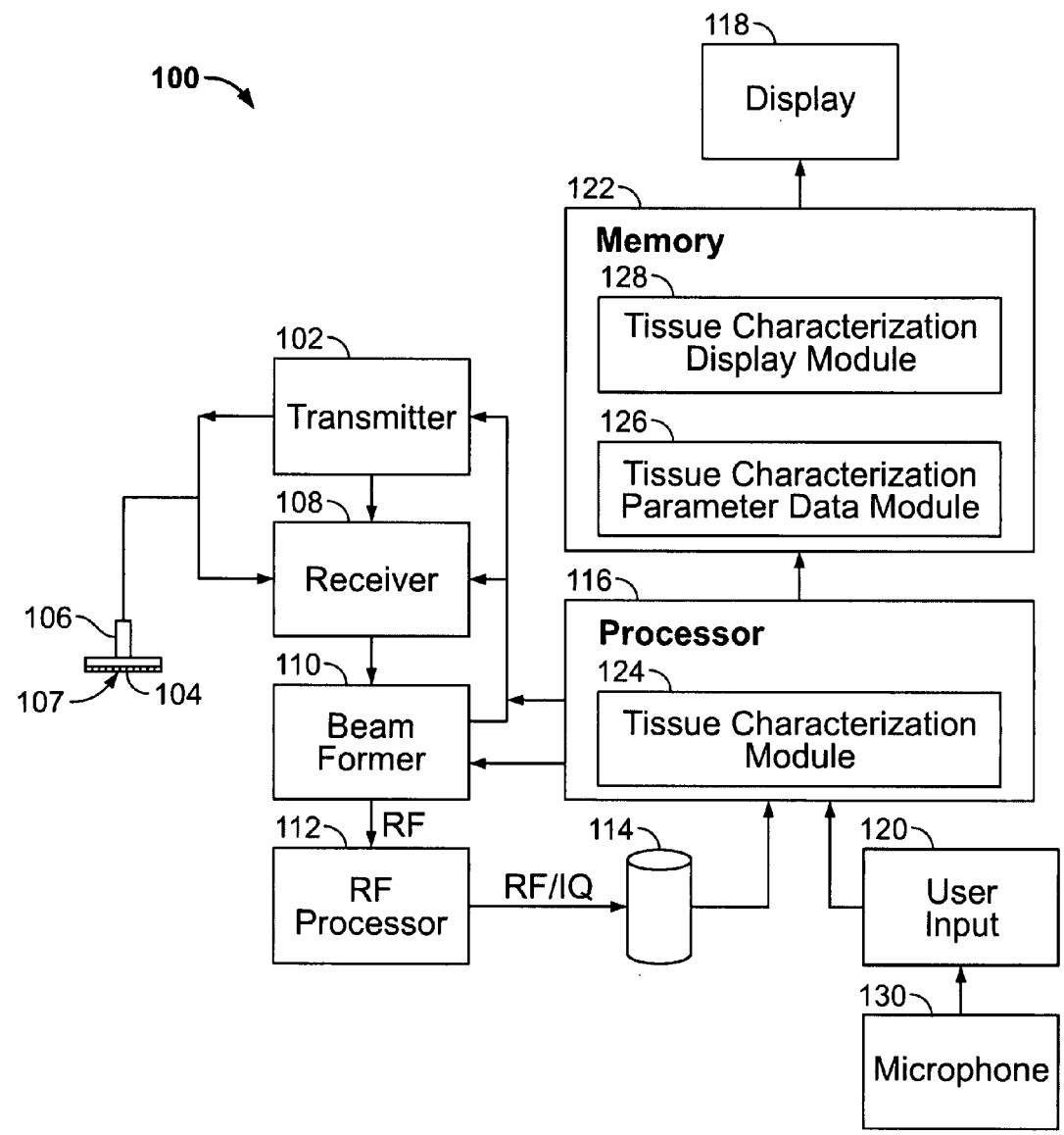
FIG. 1 illustrates a block diagram of an ultrasound system formed in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

FIG. 1 illustrates a block diagram of an ultrasound system 100. The ultrasound system 100 includes a transmitter 102 that drives transducer elements 104 within a probe 106 to emit pulsed ultrasonic signals into a body. The probe 106 has a probe face 107 typically configured to rest on the skin of a patient or outer surface of the subject being scanned. The probe 106 may be a linear probe or other probe able to perform interleaved scanning as discussed below. The ultrasonic signals or transmit beams are back-scattered from structures in the body, like blood cells or muscular tissue, to produce echoes or receive beams that return to the transducer elements 104. The returning echoes are converted by the transducer elements 104 back to electrical energy that is received by a receiver 108. The received signals are passed through a beamformer 110 that performs beamforming (combining the transducer element signals to perform steering and focusing of the beam) and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage.

A user input 120 may be used to control operation of the ultrasound system 100, including, to control the input of patient data, scan parameters, select tissue characterization to detect elasticity properties during a current scan, select and/or change how the tissue characterization is displayed, and may also include using voice commands provided via a microphone 130. Other various embodiments such as a set of user controls may be configured for controlling the ultrasound system 100 and may be provided, for example, as part of a touch screen or panel, and as manual inputs, such as user operable switches, buttons, and the like. The set of user controls may be manually operable or voice operated.

The ultrasound system 100 also includes a processor 116 to process the acquired ultrasound information (i.e., RF signal data or IQ data pairs) and prepare frames of ultrasound information for display on display 118. The processor 116 is adapted to perform one or more processing operations according to a plurality of selectable ultrasound modalities on the acquired ultrasound information. Acquired ultrasound information may be processed in real-time during a scanning session as the echo signals are received.

A tissue characterization module 124, a tissue characterization parameter data module 126 and a tissue characterization display module 128 may be used to detect property parameter differences such as stiffness that are present within tissues currently being scanned and to indicate the differences to the operator. The modules 124, 126 and 128 may be implemented in hardware or software, or a combination thereof. Tissue differences may be detected within a predetermined area based on at least the size of the linear probe 106, the depth of the image, and the like. Optionally, the operator may select a subset of the image by defining and/or modifying a region of interest (ROI) within which tissue characterization is accomplished. Optionally, the operator may input a specific depth(s) or point(s) of interest and the tissue characterization module 124 may process the image based on the operator input.

It should be understood that the functionality discussed with respect to the system 100 is not limited to any ultrasound system type. For example, the system 100 may be housed within a cart-based system or may be implemented in a smaller, portable system as shown in FIG. 2.

Figure 2:
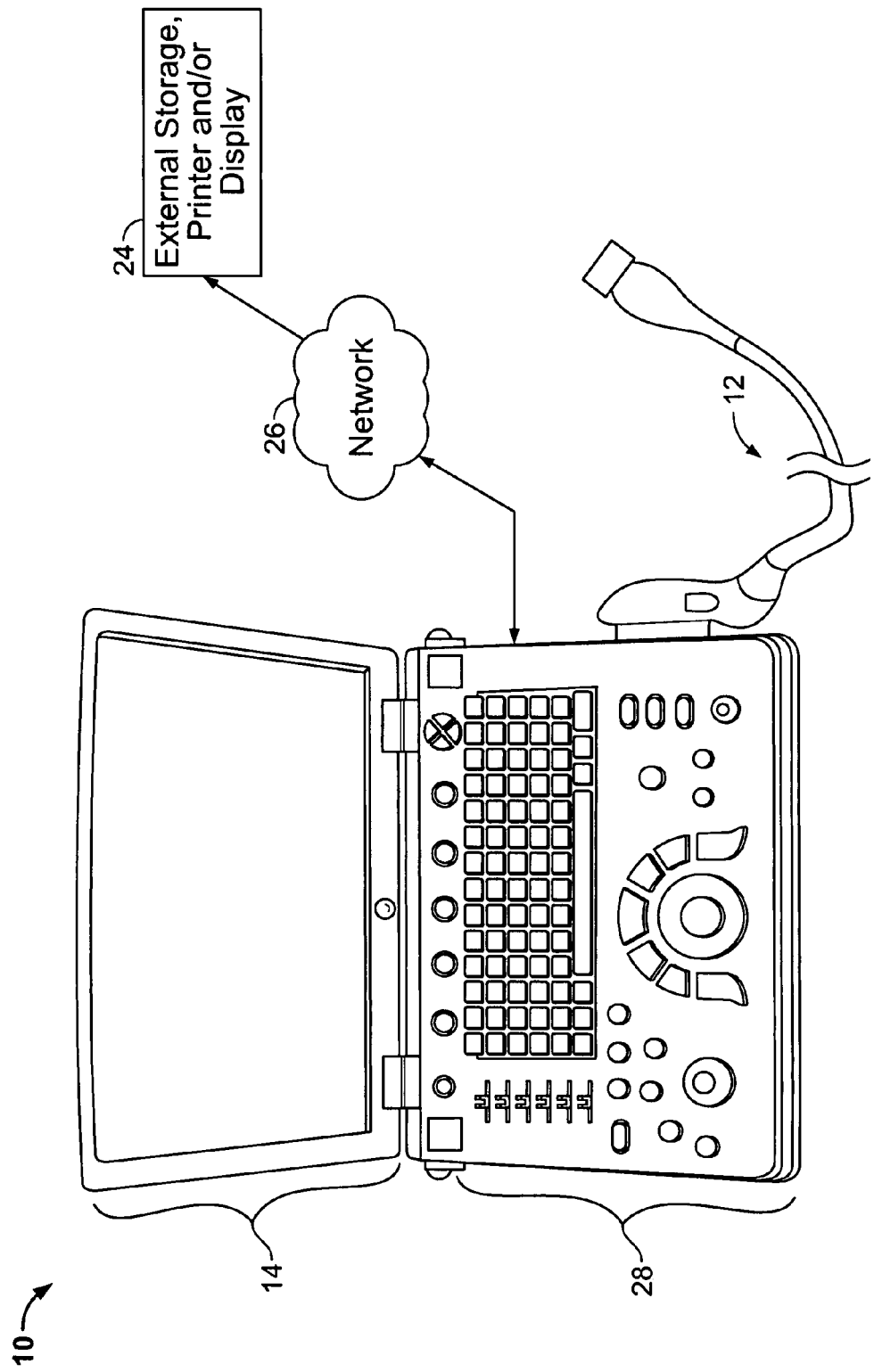
FIG. 2 illustrates a miniaturized ultrasound system having a probe configured to acquire ultrasonic data in accordance with an embodiment of the present invention.

FIG. 2 illustrates a miniaturized ultrasound system 10 having a probe 12 configured to acquire ultrasonic data. As used herein, "miniaturized" means that the ultrasound system is a handheld or hand-carried device or is configured to be carried in a person's hand, pocket, briefcase-sized case, or backpack. For example, the ultrasound system 100 may be a hand-carried device having a size of a typical laptop computer, for instance, having dimensions of approximately 2.5 inches in depth, approximately 14 inches in width, and approximately 12 inches in height. The ultrasound system 100 may weigh about ten pounds, and thus is easily portable by the operator. An integrated display 14 (e.g., an internal display) is also provided and is configured to display a medical image.

The ultrasonic data may be sent to external device 24 via a wired or wireless network (or direct connection, for example, via a serial or parallel cable or USB port) 26. In some embodiments, external device 24 may be a computer or a workstation having a display. Alternatively, external device 24 may be a separate external display or a printer capable of receiving image data from the hand carried ultrasound imaging device 10 and of displaying or printing images that may have greater resolution than the integrated display 14.

A user interface 28 (that may also include integrated display 14) is provided to receive commands from an operator. The acquired image data may be acquired in a higher resolution than that displayable on the integrated display 14.

As another example, the ultrasound device 10 may be a pocket-sized ultrasound system. By way of example, the pocket-sized ultrasound system may be approximately 2 inches wide, approximately 4 inches in length, and approximately 0.5 inches in depth and weigh less than 3 ounces. The pocket-sized ultrasound system may include a display, a user interface (i.e., keyboard) and an input/output (I/O) port for connection to the probe (all not shown). It should be noted that the various embodiments may be implemented in connection with a miniaturized ultrasound system having different dimensions, weights, and power consumption.

Figure 3:
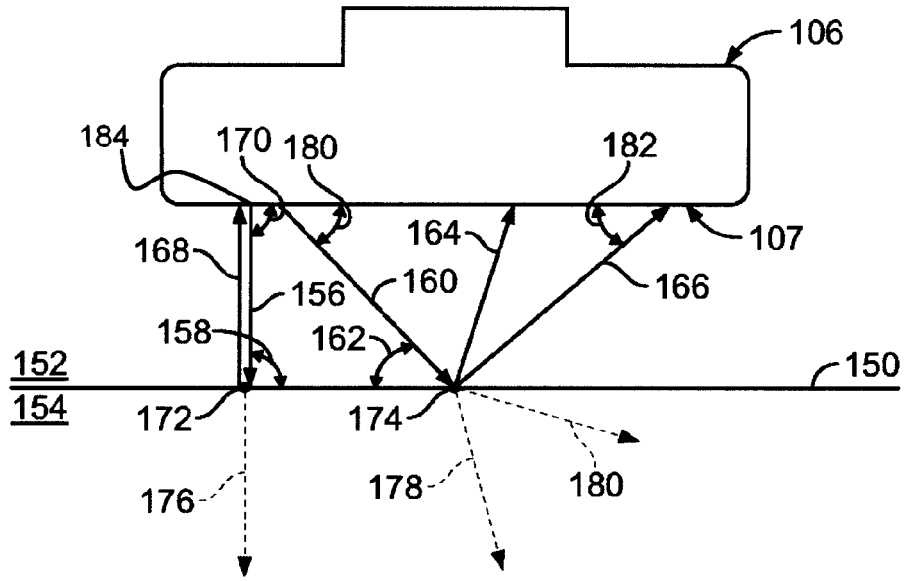
FIG. 3 illustrates an example of generating pressure waves and/or shear waves using diagnostic ultrasound scanning in accordance with an embodiment of the present invention.

FIG. 3 illustrates an example of using the probe 106 of FIG. 1 to transmit ultrasonic waves to generate pressure waves and/or shear waves. During an ultrasound examination, the operator may image tissues by transmitting beams of ultrasound energy at an approximately 90 degree angle with respect to the probe face 107. The beams or portions of the beams may also be steered to different angles with respect to the probe face 107. An interface 150 is illustrated between a first type of tissue 152 and a second type of tissue 154. By way of example, the interface 150 indicates a definite boundary such as a wall of the carotid artery or an edge of a tumor. The interface 150 may be visualized using standard ultrasound imaging. However, plaque morphology within the artery may not be specifically determined, such as whether the plaque is soft or hard plaque. Other examples are tissue characteristics of the tumor to determine properties that may be related to cancerous lesions and imaging areas of burned or otherwise damaged tissues to help determine an extent of grafting needed. In this example, the interface 150 and at least a portion of the probe face 107 are approximately planar with respect to each other.

A transmitted P-wave 156 is transmitted at an approximately 90 degree angle 170 with respect to the probe face 107 and intersects the interface 150 at normal incidence or at a 90 degree angle 158. The transmitted P-wave 156 may be, for example, a longitudinal or compressional wave. At normal incidence, reflected P-waves 168 are reflected back to the probe 106 with few or no shear waves (S-waves) being generated. Each of the reflected P-waves 168 have an amplitude component. Portions of the ultrasound energy of the transmitted P-wave 156 continue past the boundary 150 as P-wave 176.

When a transmitted P-wave 160 is transmitted at an oblique transmit angle 180 to intersect the interface 150 at an oblique angle 162, a reflected S-wave 164 and a reflected P-wave 166 result. Therefore, some of the ultrasound energy is converted to shear or S-waves. Each of the reflected P-waves 166 has an amplitude component. Portions of the ultrasound energy of the transmitted P-wave 160 continue past the boundary 150 as S-wave 178 and P-wave 180. The reflected P-wave 166 may be received by the probe 106 at a receive angle 182 that is the same magnitude as the transmit angle 180.

Although the transmitted P-wave 156, originating from transmission point or transmit origin 184, is illustrated as being located proximate to the reflected P-wave 168, it should be understood that the transmitted P-wave 156 and the reflected P-wave 168 share a common reflection point or receive origin 172. The transmitted P-wave 160, reflected S-wave 164 and the reflected P-wave 166 also share a common reflection point or receive origin 174. The common reflection points or receive origins 172 and 174 each represent a single point within the anatomy that may be described with an X, Y or X, Y, Z coordinate.

Figure 4:
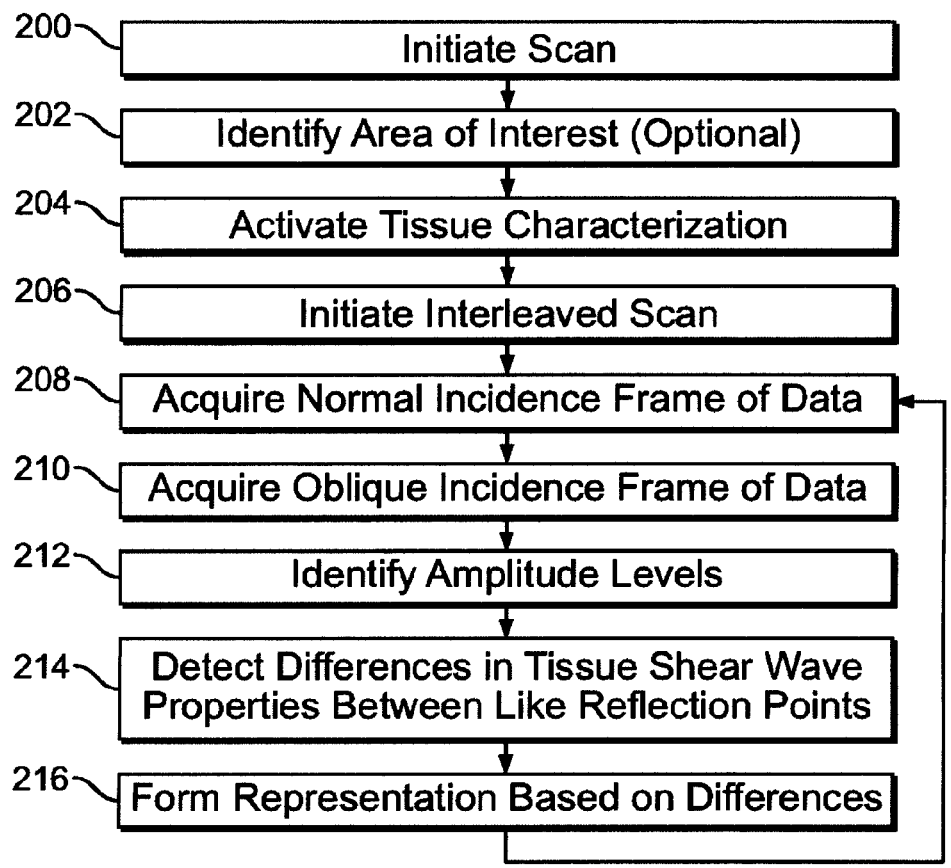
FIG. 4 illustrates a method for detecting tissue elasticity characteristics using diagnostic ultrasound scanning in accordance with an embodiment of the present invention.

FIG. 4 illustrates a method for detecting tissue elasticity characteristics using diagnostic ultrasound scanning. The method may be accomplished using the system 100 and does not rely on any external source of pressure or movement, or on an additional probe.

At 200, the operator initiates an ultrasonic scan, such as with the system 100 of FIG. 1. An image, such as a B-mode image, is displayed on the display 118. In one example, the carotid artery may be imaged. The operator may use a linear probe having a size that allows scanning of desired anatomy with oblique angles. For example, a larger probe may be needed to determine tissue elasticity of structures further from the probe face 107 compared to structures located closer to the probe face 107.

At 202, the operator may optionally identify areas or portions of anatomy within the displayed ultrasound image for tissue characterization. For example, the operator may define an ROI comprising a portion of the carotid artery and surrounding tissue, such as to determine whether calcified plaque is present. The operator may also define one or more depths within the image wherein the processor 116 defines an ROI based on the one or more depths, or within a predetermined range proximate to and/or surrounding the depth. Automatic image analysis may also be used, either alone or together with operator definitions.

At 204 the operator may use the user input 120 to select tissue characterization and thus activate the tissue characterization module 124. Optionally, the tissue characterization module 124 may be activated automatically, such as based on a selected protocol. At 206, the tissue characterization module 124 may instruct the processor 116 and/or beamformer 110 to initiate an interleaved scanning mode such that alternating frames of data may be acquired.

Figure 5:
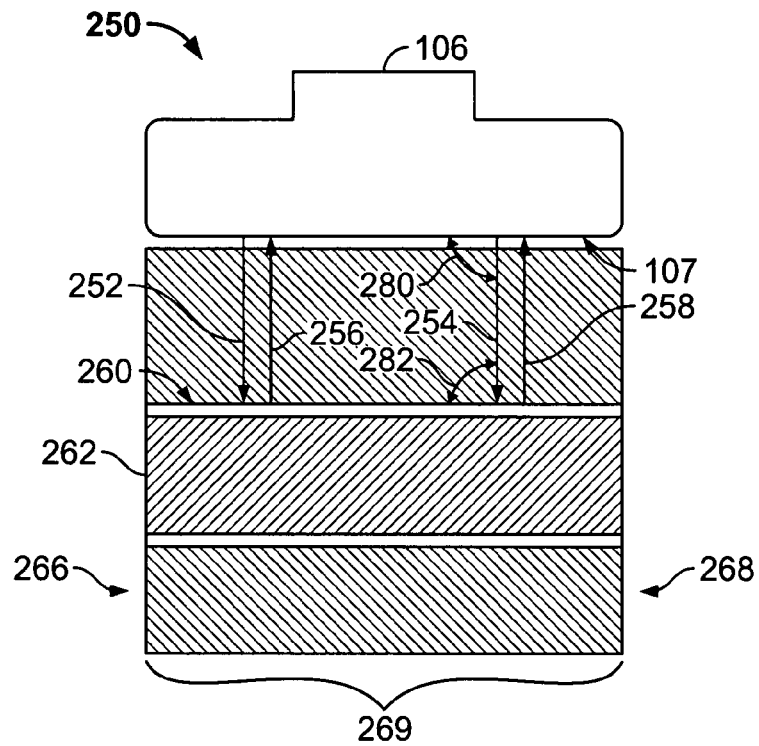
FIG. 5 illustrates a first scanning sequence used to acquire a normal incidence frame of data in accordance with an embodiment of the present invention.
Figure 6:
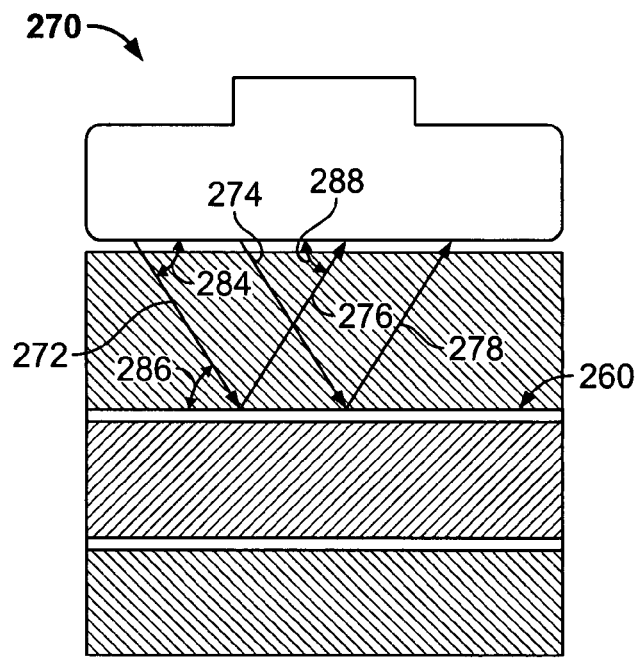
FIG. 6 illustrates a second scanning sequence used to acquire an oblique incidence frame of data in accordance with an embodiment of the present invention.

FIGS. 5 and 6 illustrate an example of acquiring interleaved scanning sequences to detect differences in stiffness within tissues being imaged. FIG. 5 generally illustrates a first scanning sequence 250 used to acquire a normal incidence frame of data and FIG. 6 generally illustrates a second scanning sequence 270 used to acquire an oblique incidence frame of data. The first and second scanning sequences 250 and 270 are accomplished with the probe 106 having the probe face 107 as shown. In this example, a carotid artery 262 may be imaged. A boundary 260 is indicated that marks a change in tissue characteristics, which in this example is an outer wall of the carotid artery 262. As discussed previously, the wall is visible to the operator using traditional ultrasound scanning, however, the hardness or morphology of the plaque is not visible to the operator. The probe face 107 and boundary 160 are approximately planar with respect to each other.

In general, ultrasound beams are transmitted and received to and from points within field of view (FOV) 269 of the probe 106 at normal and oblique angles. Therefore, limitations on determining tissue differences near side edges 266 and 268 of the FOV 269 of the probe 106 may be encountered because of the necessary transmit and receive scanning angles. However, it should be understood that angles other than a normal angle may be used with the oblique angle.

Returning to FIG. 4, at 208, the processor 116 acquires a normal incidence frame of data using the first scanning sequence 250 (as shown in FIG. 5) wherein ultrasound transmit beams 252 and 254 are transmitted having a transmit angle 280 of approximately 90 degrees with respect to the probe face 107. Because the probe face 107 and the boundary 260 are approximately parallel to each other, the transmit beams 252 and 254 interface the boundary 260 at normal incidence or at an approximate 90 degree angle 282. Although the example herein describes an angle of normal incidence, other angles may be used. Receive beams 256 and 258, respectively, are returned from the boundary 260 and detected by the probe 106. The receive beams 256 and 258 each have an amplitude component. Although only two transmit beams 252 and 254 and two receive beams 256 and 258 are shown, it should be understood that more transmit beams and receive beams may be used. Also, as discussed previously, the transmit beam 252 and receive beam 256 share a common reflection point (not shown) and the transmit beam 254 and receive beam 258 share another common reflection point (not shown). Each of the reflection points has a known coordinate location within the image or frame of data. The normal incidence frame of data may be used to display the image, such as a B-mode image, on the display 116, as well as to calculate the stiffness of the tissue associated with a particular reflection point.

At 210, the processor 116 acquires the oblique incidence frame of data using the second scanning sequence 270 (FIG. 6). The normal and oblique incidence frames of data are of the same physical structures and orientation within the patient. To acquire the oblique incidence frame of data, transmit beams 272 and 274 are transmitted at a transmit angle 284 that is other than 90 degrees with respect to the probe face 107. Therefore, the transmit beams 272 and 274 interface with the boundary 260 with oblique incidence at angle 286. Receive beams 276 and 278 interface with the probe face 107 at an oblique receive angle 288. The receive beams 276 and 278 each have an amplitude component. The beamformer 110 and processor 116 determine the transmit and receive apertures based on known transmit parameters. For example, the transmit beam 272 is transmitted at a known transmit or steer angle (the transmit angle 284) and the processor 116 may calculate an angle of incidence (angle 286) with the boundary 260 based on the assumption that the boundary 260 is planar with respect to the probe face 107. The receive angle 288 is determined as the equal and opposite oblique angle with respect to the transmit angle 284. The angle of incidence (angle 286) associated with each receive beam may be determined and may be used as described further below. In one embodiment, the transmit angle 284 and oblique receive angle 286 may be determined based on a general direction of the object or point of interest determined previously at 202.

Figure 7:
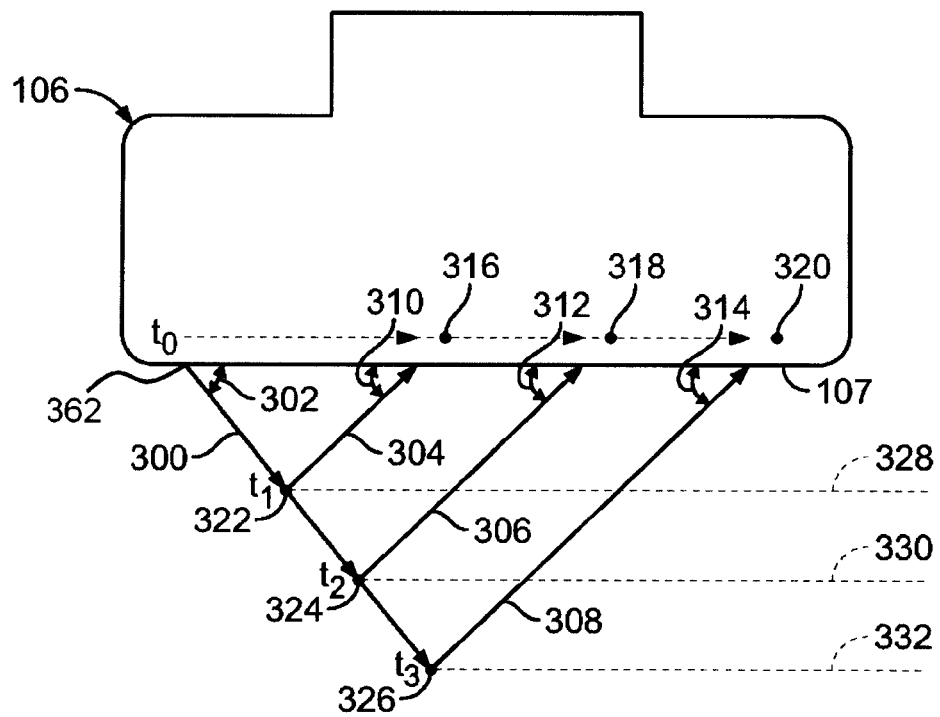
FIG. 7 illustrates another example of transmitting and receiving beams to acquire an oblique incidence frame of data in accordance with an embodiment of the present invention.

FIG. 7 illustrates another example of transmitting and receiving beams to acquire an oblique incidence frame of data. The oblique incidence frame of data covers at least a portion of the B-mode image, detecting many reflection points within the image. A transmit beam 300 is transmitted, originating from a transmission point (transmit origin) 362, at a steer angle 302. The steer angle 302 may be fixed such that a single steer angle is used for many transmit beams (not shown) across the FOV of the probe 106. For example, a steer angle 302 of approximately 45 degrees with respect to the probe face 107 may be used. Alternatively, another oblique angle may be based at least on the location of desired reflection point(s) within the FOV. It should be understood that although only one transmit beam 300 is illustrated, there are many transmit beams.

Receive beam(s) 304, 306 and 308 are fixed at receive angles 310, 312 and 314, respectively, and receive reflected ultrasound data based on the transmit beam 300. Each of the first, second, and third receive beams 304, 306 and 308 is associated with a first, second and third reflection point or receive origin 322, 324 and 326, respectively, at first, second and third depths 328, 330 and 332, respectively. Although not illustrated, many more receive beams are also used. The apex of the receive focus trajectory is dynamically moved to acquire the three received image samples from the reflection points or receive origin 322, 324, 326 and so on. In other words, the receive beams 304, 306 and 308 are snapshots of the same receive focus trajectory at different times. The receive beams 304, 306 and 308 comprise an amplitude component as discussed previously. The receive angles 310, 312 and 314 are the same with respect to each other and are equal and opposite angles with respect to the transmit steer angle 302. While dynamically focusing, a receive beam apex is translated dynamically (illustrated by apex 316, 318 and 210 associated with the first, second and third receive beams 304, 306 and 308, respectively) by the appropriate speed (e.g., t1, t2, t3) to ensure that the dynamic receive focus coincides with the transmit beam trajectory at every depth 328, 330 and 332 given the size of the probe 106.

Returning to FIG. 4, at 212 the tissue characterization module 124 identifies amplitude levels of received beams in the normal and oblique incidence frames of data. At 214, the tissue characterization module 124 detects differences in shear wave properties between reflection points that are spatially the same within the normal and oblique incidence frames of data.

In general, the magnitude of the difference between the amplitude levels represents an amount of change in shear wave properties. Receive beams or echoes returned from reflection points within tissue that is relatively the same in property, such as stiffness, will have only slight differences in amplitude when comparing the receive beam amplitudes between the normal and oblique incidence frames of data. Receive beams returned from reflection points that correspond to a boundary between tissues having different stiffnesses have greater differences in amplitude between the normal and oblique incidence frames of data. For example, a greater difference in amplitude is experienced between the carotid wall and a hard or calcified plaque deposit than between the carotid wall and a soft plaque deposit.

Detecting the differences in shear wave properties in tissues may be accomplished in multiple ways. In one embodiment, the tissue characterization module 124 may calculate a stiffness parameter using known equations associated with Amplitude versus Offset (AVO) processes. The stiffness parameter may be used as an indicator of the stiffness of the tissue at the reflection point. In another embodiment, weighted subtraction may be used, wherein the amplitudes of the second frame of data may be weighted to increase the detected difference in stiffness. The weighting may be uniform or may be based on a curve to weight greater and lesser amplitude differences differently.

In another embodiment, for each reflection point, the characterization module 124 may compare the amplitude component of the receive beams from the normal and oblique incidence frames of data to determine an amplitude magnitude difference. Variations exist within normal tissues, and thus small amplitude magnitude differences are expected even within tissues that do not experience significant changes in stiffness. Therefore, a minimum difference threshold may be predetermined, such that reflection points having amplitude magnitude differences below the minimum difference threshold may be considered as having substantially the same stiffness. The tissue characterization module 124 may then access the tissue characterization data module 126 that may be stored in the memory 122 (as shown in FIG. 1). The tissue characterization data module 126 may comprise look-up tables, charts, curves, databases and the like that take into account the amplitude magnitude differences of each of the identified receive beams, and, optionally, the angle of incidence that was determined at 210. The tissue characterization module 124 may determine a stiffness parameter for each reflection point that represents the stiffness at that point based on the predetermined data within the tissue characterization data module 126.

At 216, the tissue characterization module 124 forms a representation based on the stiffness parameter(s) and/or amplitude magnitude difference(s) determined above for each reflection point. The tissue characterization module 124 may access a tissue characterization display module 128 that may comprise look-up tables, charts, curves, databases and the like. The parameters and/or amplitude magnitude differences may be compared to previously determined values within the characterization display module 128 that each may be correlated with a display effect. For example, a parametric overlay may be formed over the current B-mode image and may use display effects such as color, intensity, patterns and/or other effects such as flashing to indicate changes in tissue stiffness.

By way of example only, a spectrum of colors may be used by the tissue characterization display module 128 to form the overlay, such that reflection points representing a low level of stiffness difference, but still above the minimum threshold (if used), are displayed in a predetermined first color such as green. The reflection points representing a high level of stiffness difference may be displayed in a predetermined second color such as red. The reflection points between the low and high levels may be represented by other colors on the spectrum.

Optionally, the stiffness parameters and/or amplitude magnitude differences may be scaled such that the least difference and the greatest difference are always displayed with the same indications, regardless of the actual range of stiffness differences. Therefore, if a small degree of difference exists between the last and greatest differences, the display effect may be used to magnify the differences, and or to weight the differences to make all differences more apparent.

The method of FIG. 4 returns to 208 to acquire additional normal and oblique incidence frames of data. Although the description herein uses two different frames, in another embodiment more than two frames with different incidence directions may be acquired and combined to detect tissue elasticity characteristics or other property parameter(s) of the scanned medium.

Figure 8:
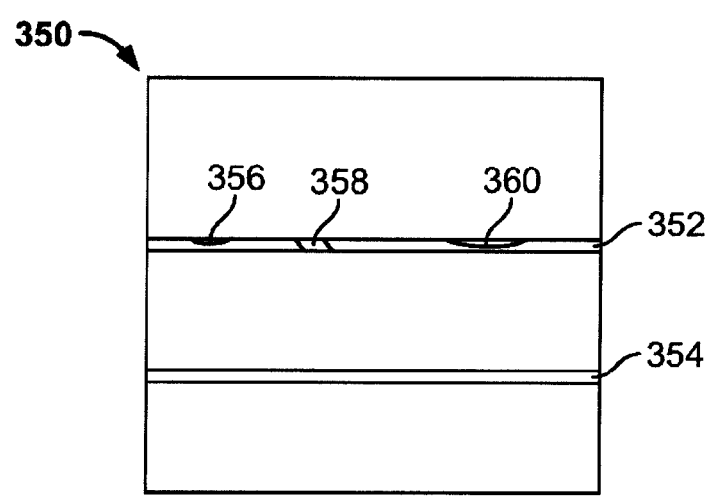
FIG. 8 illustrates a parametric overlay that may be displayed over a corresponding B-mode image to display changes in stiffness in tissues in accordance with an embodiment of the present invention.

FIG. 8 illustrates a parametric overlay 350 that may be displayed on the display 118 over the B-mode image that is based on the first data frame of FIG. 5. The parametric overlay 350 may have first and second areas 352 and 354 indicated in a first color. The first area 352 may correspond to a vessel wall and/or layer of plaque along of the carotid artery 262, the upper edge of which may correspond to the boundary 260 in FIG. 5 that was visible to the operator on the B-mode image. Additional areas within the first area 352 have been indicated, specifically, first, second and third plaque deposits 356, 358 and 360. In the B-mode image, the first, second and third plaque deposits 356, 358 and 360 and the first area 352 may have been displayed in the same way. Therefore, the operator would not be able to determine from the B-mode image the stiffness of the plaque and does not know whether the plaque is calcified or soft plaque. The overlay 350 indicates the amount of stiffness such that hard and soft plaque deposits may be indicated differently. For example, the first plaque deposit 356 may be hard plaque and thus is more stiff than the first area 352 that indicates the vessel wall. The second plaque deposit 358 may be soft plaque, and although more stiff than the first area 352, is less stiff than the first plaque deposit 356.

The overlay 350 may thus indicate the first area 352, first plaque deposit 356 and second plaque deposits 358 differently, such as with different colors, patterns, intensity and the like.

It should be understood that the differences in tissue stiffness may be displayed in other ways as well. For example, the display of the data may be interactive such that the operator may move a curser over a desired location and/or touch a location on a touch screen. The stiffness data associated with the identified location may then be displayed, such as in a numerical reference that may be scaled based on the current image or scaled based on predetermined data. Also, a report, chart or other graphical indication may be provided.

A technical effect of at least one embodiment is the ability to detect and display tissue differences related to stiffness using traditional ultrasound imaging. Frames of data are acquired at normal and oblique incidence with respect to structures in the body. The receive beams have an amplitude component that is compared between the normal and oblique incidence frames of data. A greater difference in amplitude between the two frames indicates a reflection point that creates a greater amount of shear or S-waves, indicating a tissue boundary that has a high change in stiffness between the tissues. A parametric overlay may be formed based on the amplitude differences to display the changes in stiffness to the operator.

It is to be understood that the above description is intended to be illustrative, and not restrictive. For example, the above-described embodiments (and/or aspects thereof) may be used in combination with each other. Although the descriptions herein primarily describe two different frames, it should be understood that more than two frames with different incidence directions may be acquired and combined to achieve a similar result. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An ultrasound system, comprising:
   an ultrasound probe for transmitting transmit beams and receiving receive ultrasound beams;
   a processor for controlling the ultrasound probe to direct a first plurality of transmit beams at a first angle to acquire a first incidence frame of data and a second plurality of transmit beams at a second angle to acquire a second incidence frame of data, wherein the first and second angles are different with respect to each other; and
   a tissue characterization module for comparing the first and second incidence frames of data to determine relative tissue stiffness of a scanned medium based on differences between the received ultrasound beams, wherein the tissue characterization module subtracts the first and second incident frames of data to determine the differences.

2. The system of claim 1, wherein the ultrasound probe comprises a probe face, wherein the first angle is 90 degrees with respect to the probe face and the second angle is an oblique angle with respect to the probe face.

3. The system of claim 1, further comprising:
   a tissue characterization display module for forming a representation of the differences between received diagnostic ultrasound beams; and
   a display for displaying the representation.

4. The system of claim 1, further comprising:
   a display for displaying an image based at least on the first incidence frame of data; and
   a tissue characterization display module for displaying a parametric overlay on the image based on the differences between the received diagnostic ultrasound beams.

5. The system of claim 1, wherein the processor acquires the first and second frames of data in an interleaved scanning mode.

6. The system of claim 1, wherein the ultrasound system is one of a cart-based system and a portable system.

7. A method for detecting differences in tissue, the method comprising:
   acquiring a normal incidence frame of data by using an ultrasound probe to transmit ultrasound beams at a first angle 90 degrees with respect to an ultrasound probe face;
   acquiring an oblique incidence frame of data by using the ultrasound probe to transmit ultrasound beams at a second angle that is different than the first angle, the second angle being an oblique angle with respect to the ultrasound probe face;
   determining a relative tissue stiffness of a scanned medium based on differences between receive beams for the normal and oblique incidence frames of data, wherein the differences are determined by subtracting the normal and oblique incident frames of data; and
   displaying a tissue representation based on the differences.

8. The method of claim 7, wherein acquiring the oblique incident frame of data further comprises:
   transmitting the transmit beams at the first angle with respect to the probe face; and
   receiving the receive beams at the second angle with respect to the probe face, the first and second angles being the same in magnitude and opposite in direction with respect to each other.

9. The method of claim 7, wherein the differences are associated with reflection points within each of the normal incidence frame of data and oblique incidence frame of data.

10. The method of claim 7, further comprising:
    displaying an image based on at least the normal incidence frame of data;
    determining an object boundary within the image based on one of automatic image analysis and an operator input; and
    determining transmit and receive angles with respect to the probe face, the transmit and receive angles being associated with the transmit and receive beams, respectively, and forming incidence and reflection angles, respectively, with the object boundary that are opposite with respect to each other.

11. The method of claim 7, wherein acquiring an oblique incidence frame of data further comprises:
transmitting transmit beams from a transmit origin associated with the probe face to interface with reflection points that are at different depths from the probe face;
dynamically shifting a receive origin associated with the probe face with respect to the transmit origin to form a plurality of receive origins; and
receiving the receive beams reflected from the reflection points with the plurality of receive origins, the transmit and receive beams forming a nonzero angle at the reflection points.

12. The method of claim 7, wherein the differences comprise a range of differences, the representation displaying the range of differences with a range of indicators.

13. The method of claim 7, wherein the representation displays the differences using at least one of a parametric overlay, a color overlay, a chart, and a graphical indicator responsive to an operator controlled pointer.

14. The method of claim 7, wherein at least one of the differences indicates a stiffness parameter associated with at least one reflection point in the normal and oblique incidence frames of data.

15. A method for detecting differences in tissue, the method comprising:
acquiring a normal incidence frame of data by using an ultrasound probe to transmit ultrasound beams at 90 degrees with respect to a probe face;
acquiring an oblique incidence frame of data by using the ultrasound probe to transmit ultrasound beams at a second angle different than the first angle, the second angle being an oblique angle with respect to the probe face;
displaying an image based on at least the normal incidence frame; and
displaying a tissue representation of relative tissue stiffness as a parametric overlay on the image, the parametric overlay being based on differences between the normal and oblique incidence frames of data, wherein the differences are determined by subtracting the normal and oblique incident frames of data.

16. The method of claim 15, the parametric overlay further displaying differences in a plurality of colors wherein each color represents a difference range.

17. The method of claim 15, wherein the parametric overlay further displaying the differences with a range of indicators.

18. The method of claim 15, further comprising determining amplitude differences between the normal and oblique incidence frames of data in order to determine the differences between the normal and oblique incidence frames of data.

19. The system of claim 1, wherein the tissue characterization module determines the relative tissue stiffness of the scanned medium without using a tissue elasticity model.

20. The system of claim 1, wherein the tissue characterization module determines the relative tissue stiffness of the scanned medium by calculating differences between a plurality of reflection points that are spatially located in a same position within the first and second incidence frames of data by subtracting amplitudes of the first and second incidence frames of data.

21. The system of claim 1, wherein the tissue characterization module further (i) determines a stiffness parameter of the scanned medium for a plurality of reflection points using received ultrasound beams above a minimum threshold difference of a determined amplitude magnitude difference between the received ultrasound beams and (ii) forms a representation based on the stiffness parameter to indicate changes in tissue stiffness.

22. The system of claim 1, wherein the ultrasound probe is configured to operate at diagnostic imaging ultrasound amplitudes in an ultrasound imaging scan.

23. The method of claim 11, wherein dynamically shifting a receive origin associated with the probe face with respect to the transmit origin to form a plurality of receive origins comprises dynamically moving an apex of a receive focus trajectory to acquire a plurality of samples from the reflection points with the apex translated at a speed such that a dynamic receive focus coincides with a trajectory of the transmit beams at a plurality of focus depths.

24. The method of claim 15, further comprising indicating an amount of tissue stiffness with hard and soft plaque deposits indicated differently.

25. The system of claim 1, wherein the tissue characterization module determines the relative tissue stiffness using a stiffness parameter and without using simulated data.

26. The system of claim 1, wherein the ultrasound probe comprises a probe face and at least one of the transmit beams forms an oblique angle with the probe face and generates a reflected shear way, and the processor is further configured to generate a B-mode image using the first and second incidence frames of data.

27. The system of claim 1, wherein the processor is further configured to process the incidence frames of data to generate an image for display and to calculate a tissue stiffness.

28. The system of claim 1, wherein the ultrasound probe is configured to perform diagnostic ultrasound scanning and determine the relative tissue stiffness using the transmit ultrasound beams from the diagnostic ultrasound scanning.

29. The system of claim 1, wherein at least some of the first and second plurality of transmit beams are not parallel to other ones of the first and second plurality of transmit beams.

30. The system of claim 1, wherein the transmit beams comprise ultrasound beams having an amplitude and energy for diagnostic ultrasound imaging to generate a B-mode image.

31. The method of claim 7, further comprising generating a B-mode image for display.

* * * * *